(12) United States Patent
Chen et al.

(10) Patent No.: US 12,172,031 B2
(45) Date of Patent: Dec. 24, 2024

(54) RADIOTHERAPY SYSTEM AND THERAPY PLAN GENERATION METHOD THEREFOR

(71) Applicant: NEUBORON THERAPY SYSTEM LTD., Fujian (CN)

(72) Inventors: Jiang Chen, Fujian (CN); Yi-chiao Teng, Fujian (CN); Wei-lin Chen, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 208 days.

(21) Appl. No.: 18/014,225

(22) PCT Filed: Jun. 8, 2021

(86) PCT No.: PCT/CN2021/098822
§ 371 (c)(1),
(2) Date: Jan. 3, 2023

(87) PCT Pub. No.: WO2022/001594
PCT Pub. Date: Jan. 6, 2022

(65) Prior Publication Data
US 2023/0347176 A1    Nov. 2, 2023

(30) Foreign Application Priority Data
Jul. 3, 2020   (CN) .......................... 202010630983.2

(51) Int. Cl.
*A61N 5/10*    (2006.01)

(52) U.S. Cl.
CPC ......... *A61N 5/1039* (2013.01); *A61N 5/1031* (2013.01); *A61N 2005/1034* (2013.01)

(58) Field of Classification Search
CPC ........ A61N 5/10; A61N 5/103; A61N 5/1031; A61N 5/1036; A61N 5/1037;
(Continued)

(56) References Cited

U.S. PATENT DOCUMENTS

| 5,341,292 A | 8/1994 | Zamenhof |
| 2009/0175418 A1* | 7/2009 | Sakurai ................ A61N 5/1048 |
| | | 378/98.5 |

(Continued)

FOREIGN PATENT DOCUMENTS

| CN | 104258505 A | 1/2015 |
| CN | 106853272 A | 6/2017 |

(Continued)

OTHER PUBLICATIONS

Michael William Frandsen, Rapid Geometry Interrogation for a Uniform Volume Element-Based Monte Carlo Particle Transport Simulation, 1998, Montana State University-Bozeman Bozeman, Montana.

(Continued)

*Primary Examiner* — Don K Wong
(74) *Attorney, Agent, or Firm* — Locke Lord LLP; Tim Tingkang Xia, Esq.

(57) ABSTRACT

A radiotherapy system and a therapy plan generation method therefor. The radiotherapy system includes a beam irradiation apparatus, a therapy plan module, and a control module. The beam irradiation apparatus generates a beam for therapy and irradiates an irradiated body to form an irradiated part. A tissue model template library of the irradiated body is stored in the therapy plan module; the therapy plan module performs dosage simulation calculation according to the tissue model template library, medical imaging data of the irradiated part, and a parameter of the beam for therapy generated by the beam irradiation apparatus, and generates a therapy plan. The control module retrieves, from the therapy plan module, the therapy plan corresponding to the irradiated body, and controls the beam irradiation apparatus to irradiate the irradiated body according to the therapy plan determined by the therapy plan generation method.

15 Claims, 3 Drawing Sheets

(58) Field of Classification Search
CPC .. A61N 5/1039; A61N 5/1042; A61N 5/1043; A61N 5/1045; A61N 5/1048; A61N 5/1064; A61N 5/1071; A61N 5/1075; A61N 5/1077; A61N 5/1084; A61B 6/02; A61B 6/03
See application file for complete search history.

(56) References Cited

U.S. PATENT DOCUMENTS

2017/0106210 A1  4/2017  Grodzki et al.
2018/0304099 A1  10/2018 Li et al.

FOREIGN PATENT DOCUMENTS

| CN | 106920234 A | 7/2017 |
|----|-------------|--------|
| CN | 107292075 A | 10/2017 |
| CN | 108310677 A | 7/2018 |
| CN | 108325094 A | 7/2018 |
| CN | 109308733 A | 2/2019 |
| CN | 110013613 A | 7/2019 |
| DE | 102011005739 A1 | 9/2012 |
| EP | 3357537 B1 | 9/2020 |
| EP | 4230259 A1 | 8/2023 |
| JP | 6754841 B2 | 9/2020 |

OTHER PUBLICATIONS

International Search Report of PCT/CN2021/098822, Sep. 7, 2021.

\* cited by examiner

RADIOTHERAPY SYSTEM AND THERAPY PLAN GENERATION METHOD THEREFOR

TECHNICAL FIELD

An aspect of the invention relates to a radiotherapy system, and another aspect of the invention relates to a treatment plan generation method, and in particular to a method for generating a treatment plan of a radiotherapy system.

BACKGROUND

With the development of atomics, radio therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radiotherapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example, boron neutron capture therapy (BNCT), and provides a better cancer treatment choice than traditional radioactive rays, by specific aggregation of boron-containing drugs in tumor cells in combination with precise beam regulation and control.

A three-dimensional (3D) model is widely applied to the field of analysis and simulation of scientific experiments. For example, in the field of nuclear radiation and protection, in order to simulate absorption dose of a human body under a certain radiation condition to help a doctor to formulate a treatment plan, a computer technology is usually required to perform various processing on medical imaging data, so as to establish an accurate lattice model required by Monte Carlo software, and simulation and calculation are performed in combination with Monte Carlo software. In the field of neutron capture therapy, when a lattice model required by Monte Carlo software is established according to medical imaging data, and dose calculation and evaluation are performed, basic information of organisms reflected by each lattice, such as tissue types, boron concentration information, or the like, needs to be defined in the model, and accuracy and precision of the information determine reliability of a dose calculation result. In a process of formulating the treatment plan, a large amount of time is usually consumed to delineate a region of interest (ROI) and define basic information of organisms in each region. Furthermore, a model obtained by directly converting medical imaging data is usually not accurate enough, affecting accuracy of a calculated dose distribution.

Therefore, it is necessary to provide a radiotherapy system and a method for generating a treatment plan thereof.

SUMMARY

In order to overcome defects of the related art, one aspect of the invention provides a radiotherapy system, including a beam irradiation device, a treatment plan module and a control module. The beam irradiation device generates a treatment beam and irradiates the treatment beam to an irradiated body to form an irradiated site. The treatment plan module has stored thereon a tissue model template library of the irradiated body, and performs dose simulation and calculation according to the tissue model template library, medical imaging data of the irradiated site and parameters of the treatment beam generated by the beam irradiation device, and generates treatment plans. The control module retrieves a respective one of the treatment plans corresponding to the irradiated body from the treatment plan module, and controls the beam irradiation device to irradiate the irradiated body according to the treatment plan. The tissue model template library is preset, to prevent an inaccurately established model and inaccurate dose calculation due to different personal experiences of operators such as doctors or other people; furthermore, a situation where a large amount of time and vigour are spent on definition of basic information of organisms of a lattice in the model is avoided.

Preferably, the tissue model template library may include a ROI template library providing types of ROIs required to be defined for different irradiated sites, and a material template library including a tissue type template library which defines corresponding tissue types for voxel units in each of the ROIs. The model has information of tissue types, so that elementary compositions are more accurately provided, and an established geometric model is more matched with an actual situation reflected by medical imaging data. ROI types are preset to prevent erroneous or incomplete ROI delineation due to different personal experiences of operators such as doctors or other people and thus prevent an inaccurately established model and inaccurate dose calculation; furthermore, a situation where a large amount of time and vigour are spent on selection of ROI types is avoided. Elementary compositions corresponding to each ROI and different tissue types in ROI are preset, to prevent different elementary compositions of the same ROI or the same tissue type obtained by manual giving or automatic conversion due to different personal experiences of operators such as doctors or other people and thus prevent an inaccurately established model and inaccurate dose calculation; furthermore, a situation where a large amount of time and vigour are spent on giving or conversion of elementary compositions in ROI is avoided.

Further, the treatment plan module may establish a 3D voxel prosthesis tissue model corresponding to the medical imaging data of the irradiated site according to the ROI template library and the tissue type template library, and simulate, through a Monte Carlo simulation program, a physical dose rate distribution when the irradiated site is irradiated by the treatment beam, according to the parameters of the treatment beam and the 3D voxel prosthesis tissue model.

Preferably, the material template library may include a biological effectiveness template library defining corresponding biological effectiveness data for the voxel units in each of the ROIs, and the treatment plan module may calculate an equivalent dose rate distribution when the irradiated site is irradiated by the treatment beam, according to the simulated physical dose rate distribution and biological effectiveness data of the 3D voxel prosthesis tissue model. Biological effectiveness data corresponding to each ROI and different tissue types in ROI are preset, to prevent different biological effectiveness data of the same ROI or the same tissue type given due to different personal experiences of operators such as doctors or other people and thus prevent an inaccurately established model and inaccurate dose calculation; furthermore, a situation where a large amount of time and vigour are spent on giving biological effectiveness data in ROI is avoided.

Further preferably, the radiotherapy system may be a BNCT system, the treatment plan module may define corresponding boron concentrations for the voxel units in each of the ROIs, and simulate, through the Monte Carlo simulation program, a boron dose ($D_B$), a fast neutron dose ($D_f$), a thermal neutron dose ($D_{th}$) and a photon dose ($D_\gamma$) of the 3D voxel prosthesis tissue model per unit time. The model also has information of tissue boron concentrations, so that concentration of a boron-containing drug in each tissue may be clearly known, and an actual situation may be more truly reflected when BNCT irradiation is simulated.

Further, the material template library may further include a boron concentration ratio template library defining corresponding ratios of tissue boron concentration to blood boron concentration for the voxel units in each of the ROIs.

Further, the material template library may include a biological effectiveness template library defining corresponding CBE, $RBE_f$, $RBE_{th}$ and $RBE_\gamma$ for the voxel units in each of the ROIs, and an equivalent dose rate D of the 3D voxel prosthesis tissue model is calculated by using formula 1:

$$D(Gy)=CBE(1/ppm) \times B_{con}(ppm) \times D_B(Gy) + RBE_f \times D_f(Gy) + RBE_{th} \times D_{th}(Gy) + RBE_\gamma \times D_\gamma(Gy) \quad \text{(formula 1)},$$

here CBE is a compound biological effectiveness of a boron-containing drug per unit concentration, $B_{con}$ is a tissue boron concentration, $RBE_f$ is RBE of a fast neutron, $RBE_{th}$ is RBE of a thermal neutron, and $RBE_\gamma$ is RBE of a photon.

Further, the treatment plan module may perform an optimum selection to equivalent dose rate distributions obtained by simulation and calculation according to sampling of different irradiation angles, and select at least one irradiation angle.

Preferably, the beam irradiation device may further include a collimator, the treatment plan module has stored thereon a collimator template library at least partially defining parameters of treatment beams corresponding to different collimators.

Another aspect of the invention provides a method for generating a treatment plan of a radiotherapy system, including the following operations. A 3D voxel prosthesis tissue model corresponding to medical imaging data of an irradiated site is established according to a tissue model template library. Beam parameters are defined in a Monte Carlo simulation program, and dose simulation and calculation are performed by sampling of different irradiation angles. An optimum selection is performed to the irradiation angles according to a calculation result, to generate the treatment plan. The tissue model template library is preset, to prevent an inaccurately established 3D voxel prosthesis tissue model and inaccurate dose calculation due to different personal experiences of operators such as doctors or other people; furthermore, a situation where a large amount of time and vigour are spent on definition of basic information of organisms of a lattice in the model is avoided.

Preferably, the radiotherapy system may further include a collimator, and beam parameters corresponding to different collimators are defined in the Monte Carlo simulation program according to a collimator template library.

Further preferably, the tissue model template library may include a ROI template library and a tissue type template library, and the operation of establishing the 3D voxel prosthesis tissue model corresponding to medical imaging data of the irradiated site according to the tissue model template library may include the following operations. The medical imaging data of the irradiated site is read. A 3D medical imaging voxel model is established. A ROI template library of the irradiated site is retrieved, and boundaries of ROIs provided in the ROI template library of the irradiated site are defined or read. A tissue type template library of the irradiated site is retrieved, and tissue types of voxel units in each of the ROIs are given. Tissue boron concentrations of the voxel units in each of the ROIs are given. The 3D voxel prosthesis tissue model is established. ROI types are preset to prevent erroneous or incomplete ROI delineation due to different personal experiences of operators such as doctors or other people and thus prevent an inaccurately established 3D prosthesis tissue model and inaccurate dose calculation; furthermore, a situation where a large amount of time and vigour are spent on selection of ROI types is avoided. Elementary compositions corresponding to each ROI and different tissue types in ROI are preset, to prevent different elementary compositions of the same ROI or the same tissue type obtained by manual giving or automatic conversion due to different personal experiences of operators such as doctors or other people and thus prevent an inaccurately established 3D prosthesis tissue model and inaccurate dose calculation; furthermore, a situation where a large amount of time and vigour are spent on giving or conversion of elementary compositions in ROI is avoided.

Further, the tissue model template library may include a boron concentration ratio template library, and ratios of tissue boron concentration to blood boron concentration are given for the voxel units in each of the ROIs according to a boron concentration ratio template library of the irradiated site, so that tissue boron concentrations are given for the voxel units in each of the ROIs.

Further, the operation of defining beam parameters in the Monte Carlo simulation program, and performing dose simulation and calculation by sampling of different irradiation angles may include the following operations. A physical dose received by each voxel unit of the 3D voxel prosthesis tissue model per unit time under a defined beam irradiation and at a sampled irradiation angle is simulated, the physical dose includes a boron dose ($D_B$), a fast neutron dose ($D_f$), a thermal neutron dose ($D_{th}$) and a photon dose ($D_\gamma$). An equivalent dose rate D of each voxel unit of the 3D voxel prosthesis tissue model per unit time under the defined beam irradiation is calculated by using formula 1:

$$D(Gy)=CBE(1/ppm) \times B_{con}(ppm) \times D_B(Gy) + RBE_f \times D_f(Gy) + RBE_{th} \times D_{th}(Gy) + RBE_\gamma \times D_\gamma(Gy) \quad \text{(formula 1)},$$

here CBE is a compound biological effectiveness of a boron-containing drug per unit concentration, $B_{con}$ is a tissue boron concentration, $RBE_f$ is RBE of a fast neutron, $RBE_{th}$ is RBE of a thermal neutron, and $RBE_\gamma$ is RBE of a photon, the tissue model template library includes a biological effectiveness template library, and CBE, $RBE_f$, $RBE_{th}$ and $RBE_\gamma$ are given for the voxel units in each of the ROIs according to a biological effectiveness template library of the irradiated site. Biological effectiveness data corresponding to each ROI and different tissue types in ROI are preset, to prevent different biological effectiveness data of the same ROI or the same tissue type given due to different personal experiences of operators such as doctors or other people and thus prevent an inaccurately established 3D prosthesis tissue model and inaccurate dose calculation; furthermore, a situation where a large amount of time and vigour are spent on giving biological effectiveness data in ROI is avoided.

Further, the method for generating a treatment plan may further include the following operations. An optimum selection is performed to equivalent dose rate D distributions obtained by simulation and calculation according to sampling of different irradiation angles, and at least one irradiation angle is selected.

According to the radiotherapy system and the method for generating a treatment plan of a radiotherapy system provided in the invention, accuracy of model establishment and dose calculation may be improved, and rapid formulation of the treatment plan is facilitated.

DETAILED DESCRIPTION

Embodiments of the invention will be further described in detail below with reference to the drawings, to enable those skilled in the art to implement the embodiments with reference to texts of the description.

Preferably, a neutron capture therapy system and a method for generating a treatment plan thereof are taken as the embodiments of the invention. Neutron capture therapy, especially BNCT, will be briefly described below.

Application of neutron capture therapy as an effective means for cancer treatment gradually increases in recent years, in which BNCT is most commonly seen, and neutrons supplied to BNCT may be supplied by a nuclear reactor or accelerator. The embodiments of the invention take an accelerator BNCT as an example, and basic components of the accelerator BNCT generally include an accelerator for accelerating charged particles (such as protons, deuterium cores, or the like), a target, a thermal removal system and a beam shaping body, here the accelerated charged particles act with the metal target to generate neutrons, and an appropriate nuclear reaction may be selected according to characteristics such as a desired neutron yield and energy, available energies of the accelerated charged particles, a current, physical and chemical properties of the metal target, or the like. Nuclear reactions as commonly discussed include $^{7}Li(p, n)$ $^{7}Be$ and $^{9}Be(p, n)$ $^{9}B$, both of which are endothermic reactions and have energy thresholds of 1.881 MeV and 2.055 MeV respectively. An ideal neutron source for BNCT is an epithermal neutron at a keV energy level, then theoretically, when protons with energies only slightly higher than the threshold are used to bombard a metallic lithium target, neutrons with relatively low energies may be generated for clinical application without too much retarding treatment. However, proton action sections of lithium (Li) and beryllium (Be) metallic targets with the threshold energy are not high, therefore protons with higher energies are usually selected to initiate a nuclear reaction, to generate a large enough neutron flux.

Figure 1:
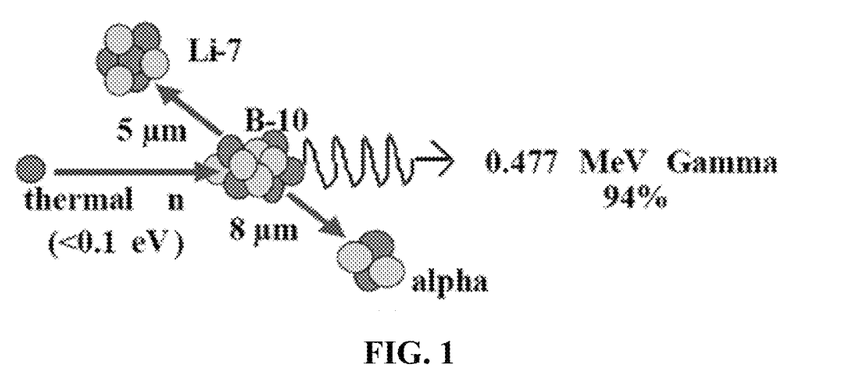
FIG. 1 is a schematic diagram of a boron neutron capture reaction.
Figure 2:
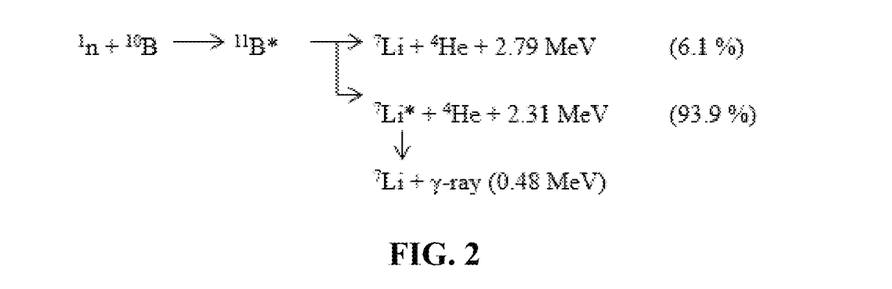
FIG. 2 is an equation of a $^{10}B(n,\alpha)$ $^{7}Li$ neutron capture nuclear reaction.

BNCT produces two heavily charged particles $^{4}He$ and $^{7}Li$ by using a characteristic of a boron ($^{10}B$)-containing drug having a high capture section for a thermal neutron, and through $^{10}B$ (n, α) $^{7}Li$ neutron capture and a nuclear fission reaction. Referring to FIGS. 1 and 2, a schematic diagram of a boron neutron capture reaction, and an equation of a $^{10}B$ (n, α) $^{7}Li$ neutron capture nuclear reaction are shown respectively, and the two charged particles have an average energy of about 2.33 MeV, and have characteristics of high linear energy transfer (LET) and short range. LET and range of α particle are 150 keV/μm and 8 μm respectively, LET and range of the heavily charged particle $^{7}Li$ are 175 keV/μm and 5 μm respectively, and the two particles have a total range approximately equivalent to a cell size, so that radiation injury to an organism may be limited to a cell level. When boron-containing drugs are selectively aggregated in tumor cells, a purpose of locally killing tumor cells may be achieved with an appropriate neutron radioactive source, on premise of not inducing too large injury to normal tissues.

A Monte Carlo method may accurately simulate collision trajectories and energy distributions of nuclear particles in a 3D space within an irradiation target. In neutron capture therapy, in order to simulate absorption dose of a human body under a certain radiation condition to help a doctor to formulate a treatment plan, a computer technology is usually required to perform various processing on medical imaging data, so as to establish an accurate lattice model required by Monte Carlo software, and simulation and calculation are performed in combination with Monte Carlo software. The medical imaging data may be magnetic resonance imaging (MRI), computed tomography (CT), positron emission tomography (PET), PET-CT or X-ray imaging. In the embodiment, data based on CT is set forth, and CT usually has a file format of DICOM. However, it is well known by those skilled in the art that other medical imaging data may also be used as long as other medical imaging data may be converted into a 3D voxel prosthesis tissue model, to be applied to the radiotherapy system and the method for generating a treatment plan thereof disclosed in the invention.

Figure 3:
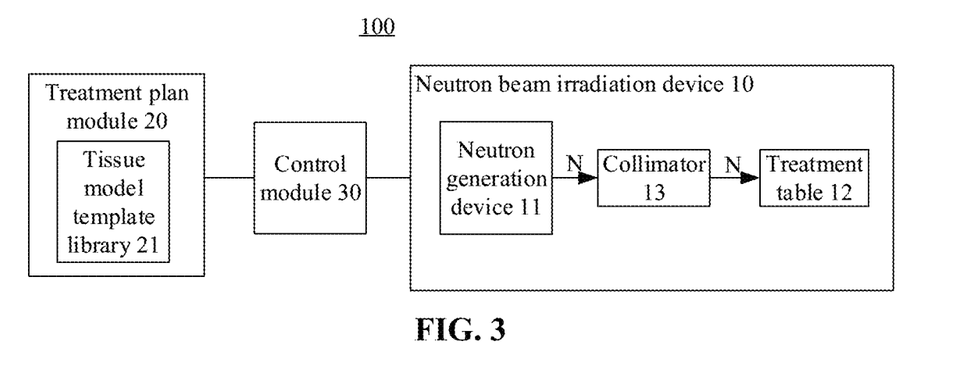
FIG. 3 is a block diagram of a neutron capture therapy system according to an embodiment of the invention.

Referring to FIG. 3, the radiotherapy system according to the embodiment is preferably a neutron capture therapy system 100, including a neutron beam irradiation device 10, a treatment plan module 20 and a control module 30. The neutron beam irradiation device 10 includes a neutron generation device 11 and a treatment table 12, and the neutron generation device 11 generates a treatment neutron beam N and irradiates the treatment neutron beam to a patient on the treatment table 12 to form an irradiated site. The treatment plan module 20 generates a treatment plan according to parameters of the neutron beam N generated by the neutron generation device 11 and medical imaging data of the irradiated site of the patient. In an embodiment, the treatment plan module 20 has stored thereon a tissue model template library 21 of the patient, the treatment plan module 20 establishes a 3D voxel prosthesis tissue model corresponding to the medical imaging data of the irradiated site according to the tissue model template library 21, and simulates and calculates, through a Monte Carlo simulation program, a dose distribution when the patient is subject to irradiation treatment, according to the parameters of the neutron beam N generated by the neutron generation device 11 and the 3D voxel prosthesis tissue model, to generate a treatment plan. The tissue model template library is preset, to prevent an inaccurately established model and inaccurate dose calculation due to different personal experiences of operators such as doctors or other people; furthermore, a situation where a large amount of time and vigour are spent on definition of basic information of organisms of a lattice in the model is avoided. The control module 30 retrieves a treatment plan corresponding to a current patient from the treatment plan module 20, and controls irradiation of the neutron beam irradiation device 10 according to the treatment plan.

Figure 4:
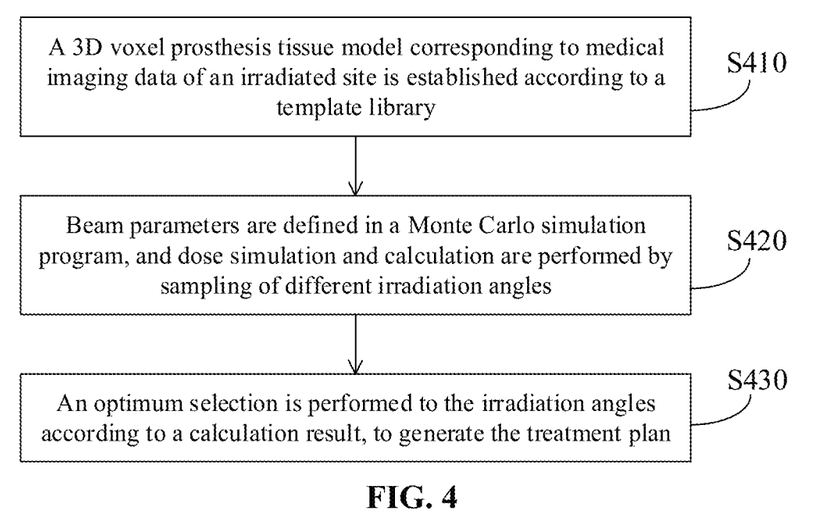
FIG. 4 is a flowchart of a method for generating a treatment plan by a treatment plan module according to an embodiment of the invention.

Referring to FIG. 4, a method for generating a treatment plan by a treatment plan module 20 according to an embodiment includes the following operations S410 to S430.

In operation S410, a 3D voxel prosthesis tissue model corresponding to medical imaging data of an irradiated site is established according to a tissue model template library 21.

In operation S420, beam parameters are defined in a Monte Carlo simulation program (such as Monte Carlo N Particle (MCNP) Transport Code), and dose simulation and calculation are performed by sampling of different irradiation angles.

In operation S430, an optimum selection is performed to the irradiation angles according to a calculation result, to generate the treatment plan.

Figure 5:
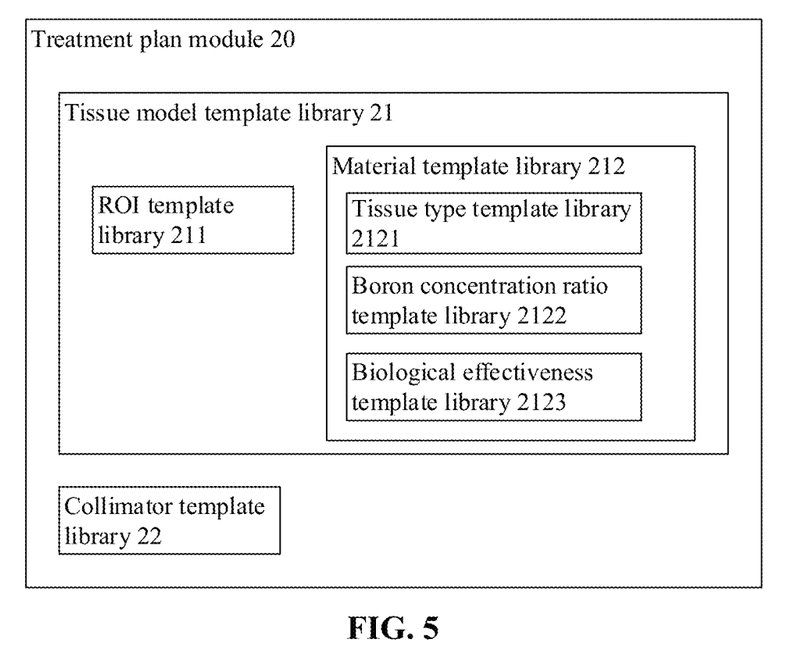
FIG. 5 is a block diagram of a treatment plan module according to an embodiment of the invention.
Figure 6:
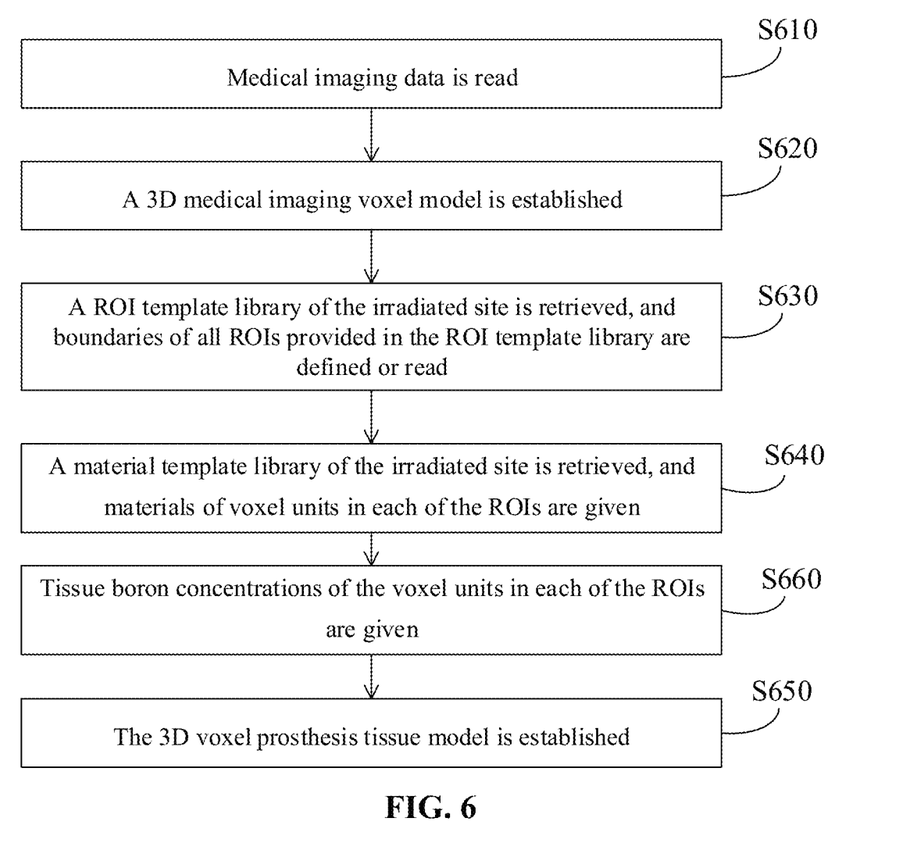
FIG. 6 is a flowchart of a method for establishing a 3D voxel prosthesis tissue model according to an embodiment of the invention.

Referring to FIG. 5, in an embodiment, the tissue model template library 21 includes a ROI template library 211 and a material template library 212, and it may be understood that the tissue model template library may also have other configurations, which is not specifically limited in the invention. Referring to FIG. 6, the operation S410 of establishing the 3D voxel prosthesis tissue model corresponding to medical imaging data of the irradiated site according to the tissue model template library 21 may further include the following operations S610 to S650.

In operation S610, the medical imaging data of the irradiated site is read.

In operation S620, a 3D medical imaging voxel model is established.

In operation S630, a ROI template library 211 of the irradiated site is retrieved, and boundaries of ROIs provided in the ROI template library 211 of the irradiated site are defined or read.

In operation S640, a material template library 212 of the irradiated site is retrieved, and materials of voxel units in each of the ROIs defined in operation S630 are given.

In operation S650, the 3D voxel prosthesis tissue model is established.

ROI refers to a region of interest, and may be a key organ, such as an eye and a liver. ROI may also be an important tissue, such as bone tissue, brain tissue, or the like. ROI may also be a tumor cell. ROI types required to be defined for different irradiated sites (different tumor types) are provided in the ROI template library, as shown in Table 1. In an embodiment, in terms of ROI required to be concerned by BNCT in a process of brain tumor treatment, all ROI types required to be defined, such as air, skin, carroid, mucosa, brain, eyeball, eyelens, gland, skeleton, soft tissue and brain tumor, are pre-created in a ROI template library of the brain tumor. In operation S630, according to ROI types provided in the retrieved ROI template library of the irradiated site, the treatment plan module 20 automatically defines or automatically reads corresponding ROI boundaries according to CT values, or the operator manually defines corresponding ROI boundaries according to CT values. By defining all ROI boundaries, a 3D medical imaging voxel model of the irradiated site is divided into different ROI regions, that is, each voxel unit is divided into a corresponding ROI region. CT values covered by some ROI regions have a wide range. In an embodiment, the treatment plan module 20 may further divide the ROI region defined in operation S630 into different tissue types according to different CT value ranges, such as brain, soft tissue, brain tumor, or the like as shown in Table 1. ROI types are preset to prevent erroneous or incomplete ROI delineation due to different personal experiences of operators such as doctors or other people and thus prevent an inaccurately established 3D prosthesis tissue model and inaccurate dose calculation; furthermore, a situation where a large amount of time and vigour are spent on selection of ROI types is avoided.

TABLE 1

ROI template library and material template library of brain tumor

| ROI type | CT value range | | tissue type | Boron concentration ratio | CBE (BPA) | $RBE_{th}$ | $RBE_f$ | $RBE_\gamma$ |
|---|---|---|---|---|---|---|---|---|
| Air | — | — | Air-OuterBody | — | — | — | — | — |
| Skin | — | — | Skin | 1 | 2.5 | 3.2 | 3.2 | 1 |
| Carotid | — | — | Carotid | 1 | 1.3 | 3.2 | 3.2 | 1 |
| Mucosa | — | — | Mucosa | 2 | 2.5 | 3.2 | 3.2 | 1 |
| Brain | −1000 | 10 | Lymph | 1 | 1.3 | 3.2 | 3.2 | 1 |
| | 10 | 15 | Brain#1 | 1 | 1.3 | 3.2 | 3.2 | 1 |
| | 15 | 25 | Brain#2 | 1 | 1.3 | 3.2 | 3.2 | 1 |
| | 25 | 30 | Brain#2 | 1 | 1.3 | 3.2 | 3.2 | 1 |
| | 30 | 40 | Brain#4 | 1 | 1.3 | 3.2 | 3.2 | 1 |
| | 40 | 50 | Brain#5 | 1 | 1.3 | 3.2 | 3.2 | 1 |
| | 50 | 3070 | Brain#6 | 1 | 1.3 | 3.2 | 3.2 | 1 |
| Eyeball | −1000 | 40 | Eyeball#1 | 1 | 1.3 | 3.2 | 3.2 | 1 |
| | 40 | 80 | Eyeball#2 | 1 | 1.3 | 3.2 | 3.2 | 1 |
| | 80 | 3070 | Eyeball#3 | 1 | 1.3 | 3.2 | 3.2 | 1 |
| Eyelens | −1000 | 80 | Eyelens#1 | 1 | 1.3 | 3.2 | 3.2 | 1 |
| | 80 | 3070 | Eyelens#2 | 1 | 1.3 | 3.2 | 3.2 | 1 |
| Gland | −1000 | 25 | Gland#1 | 1 | 1.3 | 3.2 | 3.2 | 1 |
| | 25 | 60 | Gland#2 | 1 | 1.3 | 3.2 | 3.2 | 1 |
| | 60 | 3070 | Gland#3 | 1 | 1.3 | 3.2 | 3.2 | 1 |

TABLE 1-continued

ROI template library and material template library of brain tumor

| | | | | | | | | |
|---|---|---|---|---|---|---|---|---|
| Skeleton | −1000 | 100 | Skeleton#1 | 1 | 1.3 | 3.2 | 3.2 | 1 |
| | 100 | 200 | Skeleton#2 | 1 | 1.3 | 3.2 | 3.2 | 1 |
| | 200 | 250 | Skeleton#3 | 1 | 1.3 | 3.2 | 3.2 | 1 |
| | 250 | 300 | Skeleton#4 | 1 | 1.3 | 3.2 | 3.2 | 1 |
| | 300 | 350 | Skeleton#5 | 1 | 1.3 | 3.2 | 3.2 | 1 |
| | 350 | 400 | Skeleton#6 | 1 | 1.3 | 3.2 | 3.2 | 1 |
| | 400 | 425 | Skeleton#7 | 1 | 1.3 | 3.2 | 3.2 | 1 |
| | 425 | 450 | Skeleton#8 | 1 | 1.3 | 3.2 | 3.2 | 1 |
| | 450 | 500 | Skeleton#9 | 1 | 1.3 | 3.2 | 3.2 | 1 |
| | 500 | 525 | Skeleton#10 | 1 | 1.3 | 3.2 | 3.2 | 1 |
| | 525 | 550 | Skeleton#11 | 1 | 1.3 | 3.2 | 3.2 | 1 |
| | 550 | 600 | Skeleton#12 | 1 | 1.3 | 3.2 | 3.2 | 1 |
| | 600 | 650 | Skeleton#13 | 1 | 1.3 | 3.2 | 3.2 | 1 |
| | 650 | 1200 | Skeleton#14 | 1 | 1.3 | 3.2 | 3.2 | 1 |
| | 1200 | 1700 | Skeleton#15 | 1 | 1.3 | 3.2 | 3.2 | 1 |
| | 1700 | 2800 | Skeleton#16 | 1 | 1.3 | 3.2 | 3.2 | 1 |
| | 2800 | 3070 | Skeleton#17 | 0 | 1.3 | 3.2 | 3.2 | 1 |
| Soft tissue | −1000 | −800 | Air-InnerBody | 0 | 0 | 3.2 | 3.2 | 1 |
| | −800 | −600 | Lipid | 1 | 1.3 | 3.2 | 3.2 | 1 |
| | −600 | −500 | Adipose Tissue#1 | 1 | 1.3 | 3.2 | 3.2 | 1 |
| | −500 | −300 | Adipose Tissue#2 | 1 | 1.3 | 3.2 | 3.2 | 1 |
| | −300 | −100 | Adipose Tissue#3 | 1 | 1.3 | 3.2 | 3.2 | 1 |
| | −100 | 0 | Soft Tissue #1 | 1 | 1.3 | 3.2 | 3.2 | 1 |
| | 0 | 50 | Soft Tissue #2 | 1 | 1.3 | 3.2 | 3.2 | 1 |
| | 50 | 100 | Soft Tissue #3 | 1 | 1.3 | 3.2 | 3.2 | 1 |
| | 100 | 200 | Muscle | 1 | 1.3 | 3.2 | 3.2 | 1 |
| | 200 | 3070 | Soft Tissue #4 | 1 | 1.3 | 3.2 | 3.2 | 1 |
| Brain tumor | −1000 | 10 | Brain tumor #1 | 3 | 3.8 | 3.2 | 3.2 | 1 |
| | 10 | 15 | Brain tumor #2 | 3 | 3.8 | 3.2 | 3.2 | 1 |
| | 15 | 25 | Brain tumor #3 | 3 | 3.8 | 3.2 | 3.2 | 1 |
| | 25 | 30 | Brain tumor #4 | 3 | 3.8 | 3.2 | 3.2 | 1 |
| | 30 | 40 | Brain tumor #5 | 3 | 3.8 | 3.2 | 3.2 | 1 |
| | 40 | 50 | Brain tumor #6 | 3 | 3.8 | 3.2 | 3.2 | 1 |
| | 50 | 70 | Brain tumor #7 | 3 | 3.8 | 3.2 | 3.2 | 1 |
| | 70 | 80 | Brain tumor #8 | 3 | 3.8 | 3.2 | 3.2 | 1 |
| | 80 | 100 | Brain tumor #9 | 3 | 3.8 | 3.2 | 3.2 | 1 |
| | 100 | 150 | Brain tumor #10 | 3 | 3.8 | 3.2 | 3.2 | 1 |
| | 150 | 200 | Brain tumor #11 | 3 | 3.8 | 3.2 | 3.2 | 1 |
| | 200 | 250 | Brain tumor #12 | 3 | 3.8 | 3.2 | 3.2 | 1 |
| | 250 | 3070 | Brain tumor #13 | 3 | 3.8 | 3.2 | 3.2 | 1 |

TABLE 1-continued

ROI template library and material template library of brain tumor

| ROI type | CT value range | | tissue type | Elementary composition (elements and weight percentage thereof) | | | | | | | | | | | | |
|---|---|---|---|---|---|---|---|---|---|---|---|---|---|---|---|---|
| | | | | H | C | N | O | Na | Mg | P | S | Cl | Ar | K | Ca | Fe |
| Air | — | — | Air-OuterBody | 0.0 | 0.0 | 75.5 | 23.2 | 0.0 | 0.0 | 0.0 | 0.0 | 0.0 | 1.3 | 0.0 | 0.0 | 0.0 |
| Skin | — | — | Skin | 10.0 | 20.4 | 4.2 | 64.5 | 0.2 | 0.0 | 0.1 | 0.2 | 0.3 | 0.0 | 0.1 | 0.0 | 0.0 |
| Carotid | — | — | Carotid | 10.3 | 12.1 | 3.2 | 73.4 | 0.1 | 0.0 | 0.1 | 0.2 | 0.3 | 0.0 | 0.2 | 0.0 | 0.1 |
| Mucosa | — | — | Mucosa | 10.0 | 20.4 | 4.2 | 64.5 | 0.2 | 0.0 | 0.1 | 0.2 | 0.3 | 0.0 | 0.1 | 0.0 | 0.0 |
| Brain | −1000 | 10 | Lymph | 10.8 | 4.1 | 1.1 | 83.2 | 0.3 | 0.0 | 0.0 | 0.1 | 0.4 | 0.0 | 0.0 | 0.0 | 0.0 |
| | 10 | 15 | Brain#1 | 10.7 | 9.5 | .8 | 76.7 | 0.2 | 0.0 | 0.3 | 0.2 | 0.3 | 0.0 | 0.3 | 0.0 | 0.0 |
| | 15 | 25 | Brain#2 | 10.7 | 9.5 | 1.8 | 76.7 | 0.2 | 0.0 | 0.3 | 0.2 | 0.3 | 0.0 | 0.3 | 0.0 | 0.0 |
| | 25 | 30 | Brain#2 | 10.7 | 9.5 | 1.8 | 76.7 | 0.2 | 0.0 | 0.3 | 0.2 | 0.3 | 0.0 | 0.3 | 0.0 | 0.0 |
| | 30 | 40 | Brain#4 | 10.7 | 14.5 | 2.8 | 71.2 | 0.2 | 0.0 | 0.4 | 0.2 | 0.3 | 0.0 | 0.3 | 0.0 | 0.0 |
| | 40 | 50 | Brain#5 | 10.7 | 9.5 | 1.8 | 76.7 | 0.2 | 0.0 | 0.3 | 0.2 | 0.3 | 0.0 | 0.3 | 0.0 | 0.0 |
| | 50 | 3070 | Brain#6 | 10.6 | 19.4 | 2.5 | 66.1 | 0.2 | 0.0 | 0.4 | 0.2 | 0.3 | 0.0 | 0.3 | 0.0 | 0.0 |
| Eyeball | −1000 | 40 | Eyeball#1 | 10.7 | 6.9 | 1.7 | 80.3 | 0.0 | 0.0 | 0.1 | 0.1 | 0.0 | 0.0 | 0.2 | 0.0 | 0.0 |
| | 40 | 80 | Eyeball#2 | 10.7 | 6.9 | 1.7 | 80.3 | 0.0 | 0.0 | 0.1 | 0.1 | 0.0 | 0.0 | 0.2 | 0.0 | 0.0 |
| | 80 | 3070 | Eyeball#3 | 10.7 | 6.9 | 1.7 | 80.3 | 0.0 | 0.0 | 0.1 | 0.1 | 0.0 | 0.0 | 0.2 | 0.0 | 0.0 |
| Eyelens | −1000 | 80 | Eyelens#1 | 10.6 | 11.5 | 2.2 | 75.1 | 0.1 | 0.0 | 0.1 | 0.1 | 0.1 | 0.0 | 0.1 | 0.0 | 0.0 |
| | 80 | 3070 | Eyelens#2 | 9.6 | 19.5 | 5.7 | 64.6 | 0.1 | 0.0 | 0.1 | 0.3 | 0.1 | 0.0 | 0.0 | 0.0 | 0.0 |
| Gland | −1000 | 25 | Gland#1 | 10.9 | 50.6 | 2.3 | 35.8 | 0.1 | 0.0 | 0.1 | 0.1 | 0.1 | 0.0 | 0.0 | 0.0 | 0.0 |
| | 25 | 60 | Gland#2 | 10.6 | 33.2 | 3.0 | 52.7 | 0.1 | 0.0 | 0.1 | 0.2 | 0.1 | 0.0 | 0.0 | 0.0 | 0.0 |
| | 60 | 3070 | Gland#3 | 10.2 | 15.8 | 3.7 | 69.8 | 0.1 | 0.0 | 0.1 | 0.2 | 0.1 | 0.0 | 0.0 | 0.0 | 0.0 |
| Skeleton | −1000 | 100 | Skeleton#1 | 11.5 | 64.6 | 0.7 | 23.2 | 0.0 | 0.0 | 0.0 | 0.0 | 0.0 | 0.0 | 0.0 | 0.0 | 0.0 |
| | 100 | 200 | Skeleton#2 | 10.5 | 41.4 | 3.4 | 43.9 | 0.0 | 0.0 | 0.1 | 0.2 | 0.2 | 0.0 | 0.2 | 0.0 | 0.1 |
| | 200 | 250 | Skeleton#3 | 9.6 | 9.9 | 2.2 | 74.4 | 0.5 | 0.0 | 2.2 | 0.9 | 0.3 | 0.0 | 0.0 | 0.0 | 0.0 |
| | 250 | 300 | Skeleton#4 | 8.5 | 40.4 | 2.8 | 36.7 | 0.1 | 0.1 | 3.4 | 0.2 | 0.2 | 0.0 | 0.1 | 7.4 | 0.1 |
| | 300 | 350 | Skeleton#5 | 7.9 | 38.5 | 2.2 | 36.2 | 0.1 | 0.1 | 4.4 | 0.1 | 0.1 | 0.0 | 0.0 | 10.4 | 0.0 |
| | 350 | 400 | Skeleton#6 | 7.4 | 30.2 | 3.7 | 43.8 | 0.0 | 0.1 | 4.5 | 0.2 | 0.1 | 0.0 | 0.1 | 9.8 | 0.1 |
| | 400 | 425 | Skeleton#7 | 7.0 | 34.5 | 2.8 | 36.8 | 0.1 | 0.1 | 5.5 | 0.2 | 0.3 | 0.0 | 0.0 | 12.9 | 0.0 |
| | 425 | 450 | Skeleton#8 | 7.0 | 28.7 | 3.8 | 43.7 | 0.0 | 0.1 | 5.1 | 0.2 | 0.1 | 0.0 | 0.1 | 11.1 | 0.1 |
| | 450 | 500 | Skeleton#9 | 6.6 | 27.1 | 3.8 | 43.5 | 0.1 | 0.1 | 5.8 | 0.3 | 0.1 | 0.0 | 0.1 | 12.5 | 0.0 |
| | 500 | 525 | Skeleton#10 | 6.4 | 26.3 | 3.9 | 43.6 | 0.1 | 0.1 | 6.0 | 0.3 | 0.1 | 0.0 | 0.1 | 13.1 | 0.0 |
| | 525 | 550 | Skeleton#11 | 6.3 | 26.1 | 3.9 | 43.6 | 0.1 | 0.1 | 6.1 | 0.2 | 0.1 | 0.0 | 0.1 | 13.3 | 0.0 |
| | 550 | 600 | Skeleton#12 | 6.0 | 31.4 | 3.1 | 36.9 | 0.1 | 0.1 | 7.0 | 0.2 | 0.0 | 0.0 | 0.0 | 15.2 | 0.0 |
| | 600 | 650 | Skeleton#13 | 5.6 | 23.5 | 4.0 | 43.4 | 0.1 | 0.1 | 7.2 | 0.3 | 0.1 | 0.0 | 0.1 | 15.6 | 0.0 |
| | 650 | 1200 | Skeleton#14 | 5.0 | 21.2 | 4.0 | 43.5 | 0.1 | 0.2 | 8.1 | 0.3 | 0.0 | 0.0 | 0.0 | 17.6 | 0.0 |
| | 1200 | 1700 | Skeleton#15 | 4.6 | 19.9 | 4.1 | 43.5 | 0.1 | 0.2 | 8.6 | 0.3 | 0.0 | 0.0 | 0.0 | 18.7 | 0.0 |
| | 1700 | 2800 | Skeleton#16 | 3.4 | 15.5 | 4.2 | 43.5 | 0.1 | 0.2 | 10.3 | 0.3 | 0.0 | 0.0 | 0.0 | 22.5 | 0.0 |
| | 2800 | 3070 | Skeleton#17 | 0.2 | 0.0 | 0.0 | 41.4 | 0.0 | 0.0 | 18.5 | 0.0 | 0.0 | 0.0 | 0.0 | 39.9 | 0.0 |
| Soft tissue | −1000 | −800 | Air-InnerBody | 10.3 | 10.5 | 3.1 | 74.9 | 0.2 | 0.0 | 0.2 | 0.3 | 0.3 | 0.0 | 0.2 | 0.0 | 0.0 |
| | −800 | −600 | Lipid | 11.8 | 77.3 | 0.0 | 10.9 | 0.0 | 0.0 | 0.0 | 0.0 | 0.0 | 0.0 | 0.0 | 0.0 | 0.0 |
| | −600 | −500 | Adipose Tissue#1 | 11.6 | 68.1 | 0.2 | 19.8 | 0.1 | 0.0 | 0.0 | 0.1 | 0.1 | 0.0 | 0.0 | 0.0 | 0.0 |
| | −500 | −300 | Adipose Tissue#2 | 11.4 | 59.8 | 0.7 | 27.8 | 0.1 | 0.0 | 0.0 | 0.1 | 0.1 | 0.0 | 0.0 | 0.0 | 0.0 |
| | −300 | −100 | Adipose Tissue#3 | 11.2 | 51.7 | 1.3 | 35.5 | 0.1 | 0.0 | | 0.1 | | | 0.0 | 0.0 | 0.0 |
| | −100 | 0 | Soft Tissue #1 | 10.1 | 11.1 | 2.6 | 76.2 | 0.0 | 0.0 | 0.0 | 0.0 | 0.0 | 0.0 | 0.0 | 0.0 | 0.0 |
| | 0 | 50 | Soft Tissue #2 | 10.6 | 31.5 | 2.4 | 54.7 | 0.1 | 0.0 | 0.0 | 0.2 | 0.1 | 0.0 | 0.2 | 0.0 | 0.0 |
| | 50 | 100 | Soft Tissue #3 | 10.5 | 25.6 | 2.7 | 60.2 | 0.1 | 0.0 | 0.2 | 0.3 | 0.2 | 0.0 | 0.2 | 0.0 | 0.0 |
| | 100 | 200 | Muscle | 10.2 | 14.3 | 3.4 | 71.0 | 0.1 | 0.0 | 0.2 | 0.3 | 0.1 | 0.0 | 0.4 | 0.0 | 0.0 |
| | 200 | 3070 | Soft Tissue #4 | 9.6 | 9.9 | 2.2 | 74.4 | 0.5 | 0.0 | 2.2 | 0.9 | 0.3 | 0.0 | 0.0 | 0.0 | 0.0 |
| Brain tumor | −1000 | 10 | Brain tumor #1 | 10.8 | 4.1 | 1.1 | 83.2 | 0.3 | 0.0 | 0.0 | 0.1 | 0.4 | 0.0 | 0.0 | 0.0 | 0.0 |
| | 10 | 15 | Brain tumor #2 | 10.7 | 9.5 | 1.8 | 76.7 | 0.2 | 0.0 | 0.3 | 0.2 | 0.3 | 0.0 | 0.3 | 0.0 | 0.0 |
| | 15 | 25 | Brain tumor #3 | 10.7 | 9.5 | 1.8 | 76.7 | 0.2 | 0.0 | 0.3 | 0.2 | 0.3 | 0.0 | 0.3 | 0.0 | 0.0 |
| | 25 | 30 | Brain tumor #4 | 10.7 | 14.5 | 1.8 | 76.7 | 0.2 | 0.0 | 0.3 | 0.2 | 0.3 | 0.0 | 0.3 | 0.0 | 0.0 |
| | 30 | 40 | Brain tumor #5 | 10.7 | 9.5 | 2.2 | 71.2 | 0.2 | 0.0 | 0.4 | 0.2 | 0.3 | 0.0 | 0.3 | 0.0 | 0.0 |
| | 40 | 50 | Brain tumor #6 | 10.7 | 9.5 | 1.8 | 76.7 | 0.2 | 0.0 | 0.3 | 0.2 | 0.3 | 0.0 | 0.3 | 0.0 | 0.0 |

TABLE 1-continued

ROI template library and material template library of brain tumor

| | | | | | | | | | | | | | | | |
|---|---|---|---|---|---|---|---|---|---|---|---|---|---|---|---|
| 50 | 70 | Brain tumor #7 | 10.6 | 19.4 | 2.5 | 66.1 | 0.2 | 0.0 | 0.4 | 0.2 | 0.3 | 0.0 | 0.3 | 0.0 | 0.0 |
| 70 | 80 | Brain tumor #8 | 9.6 | 9.9 | 2.2 | 74.4 | 0.5 | 0.0 | 2.2 | 0.2 | 0.3 | 0.0 | 0.0 | 0.0 | 0.0 |
| 80 | 100 | Brain tumor #9 | 8.5 | 40.4 | 2.8 | 36.7 | 0.1 | 0.1 | 3.4 | 0.2 | 0.2 | 0.0 | 0.1 | 7.4 | 0.0 |
| 100 | 150 | Brain tumor #10 | 7.9 | 38.5 | 2.2 | 36.2 | 0.1 | 0.1 | 4.4 | 0.1 | 0.1 | 0.0 | 0.0 | 10.4 | 0.0 |
| 150 | 200 | Brain tumor #11 | 7.4 | 30.2 | 3.7 | 43.8 | 0 | 0.1 | 4.5 | 0.2 | 0.1 | 0.0 | 0.1 | 9.8 | 0.1 |
| 200 | 250 | Brain tumor #12 | 7.0 | 34.5 | 2.8 | 36.8 | 0.1 | 0.1 | 5.5 | 0.2 | 0.1 | 0.0 | 0.0 | 12.9 | 0.0 |
| 250 | 3070 | Brain tumor #13 | 7.0 | 28.7 | 3.8 | 43.7 | 0.0 | 0.1 | 5.1 | 0.2 | 0.1 | 0.0 | 0.1 | 11.1 | 0.1 |

As shown in FIG. 5, in an embodiment, the material template library 212 includes a tissue type template library 2121 which defines tissue types (elementary compositions) corresponding to the ROI region, for voxel units in each of the ROIs. Operation S640 includes the following operations. According to the tissue type template library 2121, tissue types are given for voxel units in each of the ROIs defined in operation S630. Table 1 also shows one or more tissue types (elementary compositions) corresponding to different ROIs in the ROI template library of the brain tumor. The 3D prosthesis tissue model has information of tissue types, so that elementary compositions are more accurately provided, and an established geometric model is more matched with an actual situation reflected by medical imaging data. Elementary compositions corresponding to each ROI and different tissue types in ROI are preset, to prevent different elementary compositions of the same ROI or the same tissue type obtained by manual giving or automatic conversion due to different personal experiences of operators such as doctors or other people and thus prevent an inaccurately established 3D prosthesis tissue model and inaccurate dose calculation; furthermore, a situation where a large amount of time and vigour are spent on giving or conversion of elementary compositions in ROI is avoided.

When the radiotherapy system is a BNCT system, the operation S410 of establishing the 3D voxel prosthesis tissue model corresponding to medical imaging data of the irradiated site according to the tissue model template library 21 may further include operation S660 after operation S640. In operation S660, tissue boron concentrations are given for the voxel units in each of the ROIs defined in operation S630. It may be understood that operation S660 may also occur before operation S640. Non-uniform boron concentration distribution information of each tissue organ may be obtained through real-time measurement of PET or the like, to give a boron concentration value of each voxel unit. Furthermore, the boron concentration value of each voxel unit may be given by measuring a blood boron concentration and giving ratios of tumor, tissue boron concentrations to the blood boron concentration, to establish uniform boron concentration distribution information. As shown in FIG. 5, in an embodiment, the material template library 212 further includes a boron concentration ratio template library 2122 which defines a ratio of corresponding tissue boron concentration to blood boron concentration for the voxel units in each of the ROIs. For example, Table 1 shows boron concentration ratios corresponding to different ROIs in the ROI template library of the brain tumor and different tissue types in the same ROI. A geometric model is marked with the tissue boron concentration information, so that concentration of a boron-containing drug in each tissue may be clearly known, and an actual situation may be more truly reflected when neutron irradiation is simulated.

Figure 7:
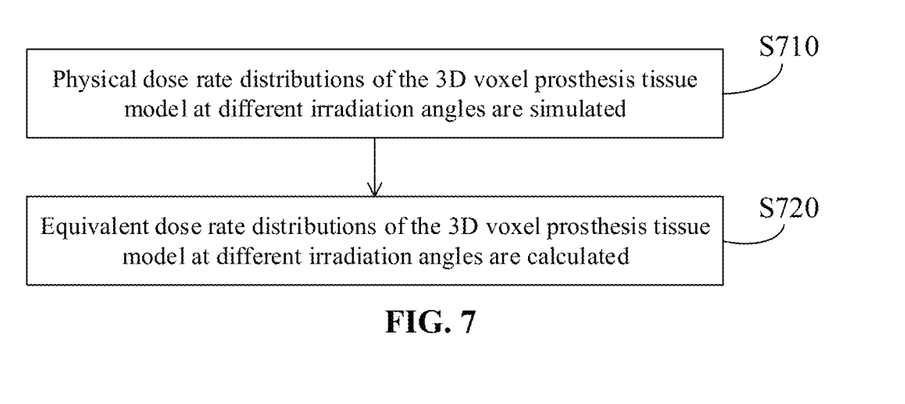
FIG. 7 is a flowchart of a method for dose simulation and calculation according to an embodiment of the invention.

After the 3D voxel prosthesis tissue model with the tissue type and the tissue boron concentration is established, collision trajectories and energy distributions of nuclear particles in an internal 3D space when the patient is irradiated by a neutron beam in BNCT may be simulated through a Monte Carlo simulation program, that is, a physical dose rate distribution may be simulated, an equivalent dose rate distribution is calculated according to the physical dose rate distribution, and then a treatment plan scheme is screened according to a dose index. Referring to FIG. 7, specifically, operation S420 includes the following operations S710 and S720.

In operation S710, beam parameters (such as beam energy, intensity, radius, or the like) are defined in a Monte Carlo simulation program, and physical dose rate distributions of the 3D voxel prosthesis tissue model at different irradiation angles are simulated by sampling of different irradiation angles, that is, a physical dose received by each voxel unit of the 3D voxel prosthesis tissue model per unit time under a defined beam irradiation and at a sampled irradiation angle is simulated.

During sampling, a starting position and a beam angle of beam calculation are required to be determined, and the starting position and angle during calculation may be determined by a forward algorithm or a reverse algorithm. In the forward algorithm, the starting position is determined as an in-vitro position, and sampling and calculation may be sequentially performed according to a fixed angle or distance interval, or may also be performed in a random sampling manner; the beam angle may be set as a direction of vector from an irradiation point to a centroid or deepest part of the tumor, and a specific endpoint position of the tumor may be adjusted according to user requirements. In the reverse algorithm, the starting position is determined in a range of the tumor, may be a centroid or deepest part of the tumor, or a random point in the range of the tumor, and the beam angle may be set by randomly sampling or sampling according to a specified interval.

During sampling, beam angles may also be screened, for example, beam angle evaluation is performed, and a beam angle for subsequent calculation is selected according to an evaluation result. Furthermore, beam angles are screened after sampling and calculation, for example, screening is performed according to a result of radiation dose distribution or a result of beam angle evaluation. A method for evaluating beam angles is not described in detail here, and may refer to a patent application published on Jun. 16, 2017 with a publication number CN 106853272 A, and entitled "METHOD FOR EVALUATING BEAM IRRADIATION ANGLES", which is incorporated here by reference in its entirety.

As shown in FIG. 3, in an embodiment, the neutron beam irradiation device 10 further includes a collimator 13. Different collimators may be selected for different patients to match with the irradiated site, so that parameters and irradiation angles of beams irradiated to the patient from outlets of the collimators are also different. While Monte Carlo simulation is performed in operation S710, a model of a selected collimator may be established. As shown in FIG. 5, in an embodiment, the treatment plan module 20 may further have stored thereon a collimator template library 22 at least partially defining parameters of beams corresponding to different collimators. When Monte Carlo simulation is performed in operation S710, collimator type may also be manually selected or automatically read, and beam parameters corresponding to corresponding collimator types are retrieved from the collimator template library.

Major factors for dose contribution in BNCT have four parts:

1) Boron dose $D_B$: coming from $\alpha$, $^7$Li particles with high LET resulting from a $^{10}$B (n, $\alpha$) $^7$Li neutron capture reaction of a boron-containing drug in a tissue and tumor with neutrons.
2) Fast neutron dose $D_f$: mainly caused by rebound protons generated by an elastic scattering effect of an epithermal fast neutron and hydrogen.
3) Thermal neutron dose $D_{th}$: a major dose resulting from protons generated by a $^{14}$N (n, p) $^{14}$C action and rebound carbon ions.
4) Photon dose $D_\gamma$: containing action of neutrons with a shielding structure, and a capture reaction with human tissues to induce photons, and the latter mainly generates 2.22 MeV photons by a $^1$H (n, $\gamma$) $^2$H reaction of thermal neutrons.

In operation S710, the physical dose received per unit time includes a boron dose ($D_B$), a fast neutron dose ($D_f$), a thermal neutron dose ($D_{th}$) and a photon dose ($D_\gamma$) per unit time obtained by simulation through the Monte Carlo simulation program.

In operation S720, equivalent dose rate distributions of the 3D voxel prosthesis tissue model at different irradiation angles are calculated.

In BNCT, due to different biological effectiveness caused by photons and neutrons, RBE of different tissues are multiplied for dose items of fast neutron, thermal neutron and photon respectively, to obtain an equivalent dose. In terms of boron dose, due to each of $\alpha$, $^7$Li particles having a short, injury is usually limited to an occurrence position of boron neutron capture action, and different types of cells have different capabilities of absorbing boron-containing drugs, so that boron concentration is not uniformly distributed in vivo. In order to obtain an equivalent dose, the dose item must be multiplied by CBE of each tissue and boron concentrations in different tissues (defined in operation S660), that is, an equivalent dose rate D of a voxel unit is calculated by using formula 1:

$$D(Gy)=CBE(1/ppm) \times B_{con}(ppm) \times D_B(Gy)+RBE_f \times D_f(Gy)+RBE_{th} \times D_{th}(Gy)+RBE_\gamma \times D_\gamma(Gy) \quad \text{(formula 1)},$$

here CBE is a compound biological effectiveness of a boron-containing drug per unit concentration, $B_{con}$ is a tissue boron concentration, $RBE_f$ is RBE of a fast neutron, $RBE_{th}$ is RBE of a thermal neutron, and $RBE_\gamma$ is RBE of a photon.

As shown in FIG. 5, in an embodiment, the material template library 212 further includes a biological effectiveness template library 2123, which defines, for the voxel units of each of the ROIs, biological effectiveness of a tissue corresponding to the ROI region on the treatment beam for treatment, due to different biological effectiveness caused by the beam to different tissues. Operation S640 further includes the following operations. A biological effectiveness template library of the irradiated site is retrieved, and biological effectiveness values are given for voxel units in each of the ROIs defined in operation S630, according to the biological effectiveness template library. In an embodiment in which the radiotherapy system is a BNCT system, the biological effectiveness template library 2123 defines, for the voxel units of each ROI, CBE, $RBE_f$, $RBE_{th}$ and $RBE_\gamma$ corresponding to the ROI region. Table 1 shows CBE, $RBE_f$, $RBE_{th}$ and $RBE_\gamma$ corresponding to different ROIs in the ROI template library of the brain tumor and different tissue types in the same ROI, here biological effectiveness of photon is used as a reference, that is, $RBE_\gamma$ is 1. The operation of giving the biological effectiveness values for the voxel units in each of the ROIs defined in operation S630 include giving CBE, $RBE_f$, $RBE_{th}$ and $RBE_\gamma$ for the voxel units in each of the ROIs defined in operation S630. A process of giving CBE may also include manually selecting a $^{10}$B-containing drug type, and different drug types correspond to different CBE. As an embodiment, CBE in Table 1 is given by taking BPA as a $^{10}$B-containing drug. It may be understood that the operation of giving biological effectiveness values may also be performed in operation S720. Biological effectiveness data corresponding to each ROI and different tissue types in ROI are preset, to prevent different biological effectiveness data of the same ROI or the same tissue type given due to different personal experiences of operators such as doctors or other people and thus prevent an inaccurately established 3D prosthesis tissue model and inaccurate dose calculation; furthermore, a situation where a large amount of time and vigour are spent on giving biological effectiveness data in ROI is avoided.

In operation S430, according to the equivalent dose rate distribution calculated in operation S720, different treatment plan solutions (irradiation angles and corresponding irradiation time) are evaluated or optimized in combination with a mathematical algorithm. For example, a ROI region is selected as a target, irradiation time corresponding to a sampled irradiation angle is obtained by taking a maximum dose, an average dose, a prescription dose or the like of the ROI region as constraint conditions, an equivalent dose distribution of the 3D voxel prosthesis tissue model at the sampled irradiation angle is obtained at the irradiation time, and then equivalent dose distributions obtained by simulating and calculating in the 3D voxel prosthesis tissue model at different irradiation angles and corresponding irradiation time are evaluated or optimized by using a dose volume histogram (DVH), an isodose curve, a dose table or the like.

The irradiation angle evaluation as described above may also be performed to evaluate, so that an operator such as a doctor or another person selects a treatment plan solution which meets requirements better. It may be understood that at least two irradiation angles may also be selected through an optimization algorithm or the like to sequentially irradiate the patient, a specific number of irradiation angles may be manually set, or may be automatically obtained through an algorithm, or arc-shaped continuous regulation and control of irradiation angles may be used, and sampling of the irradiation angle may be performed on the same side or opposite side of the patient.

It may be understood that the tissue model template library is not limited to configurations of the embodiments described in the invention, for example, it may include any one or more of an ROI template library, a tissue type template library, a boron concentration ratio template library, or a biological effectiveness template library. In a process of formulating a treatment plan, ROI types of different irradiation sits set in the retrieved tissue model template library, elementary compositions of the voxel units in each of the ROIs, boron concentration ratios of the voxel units in each of the ROIs, and biological effectiveness values of the voxel units in each of the ROIs may be manually corrected to adapt to different conditions. It may be understood that some simple transformations of the formula 1 and dose calculation, evaluation and optimum selection methods still fall within the scope of the invention.

It may be understood that the invention may also be applied to other radiotherapy fields which is well known by those skilled in the art and may be simulated by Monte Carlo software, such as proton, heavy ion, X-ray or gamma ray therapy, or the like, and the neutron beam irradiation device is another radiation beam irradiation device; and the invention may also be applied to other diseases which may be treated with irradiation of radioactive rays, such as Alzheimer's disease and rheumatoid arthritis, and tumor cells are other lesion tissues, and the patient may also be another irradiated body.

While the illustrative specific implementations of the invention have been described as above, so that those skilled in the art understand the invention, it should be apparent that the invention is not limited to the scope of the specific implementations, various changes are apparent for those skilled in the art and fall within the scope of protection of the invention, as long as these changes fall within the spirit and scope of the invention as defined and determined by the appended claims.

The invention claimed is:

1. A radiotherapy system, characterized in that the radiotherapy system comprises:
   a beam irradiation device generating a treatment beam and irradiating the treatment beam to an irradiated body to form an irradiated site;
   a treatment plan module having stored thereon a tissue model template library of the irradiated body, and performing dose simulation and calculation according to the tissue model template library, medical imaging data of the irradiated site and parameters of the treatment beam generated by the beam irradiation device, and generating treatment plans; and
   a control module retrieving a respective one of the treatment plans corresponding to the irradiated body from the treatment plan module, and controlling the beam irradiation device to irradiate the irradiated body according to the treatment plan.

2. The radiotherapy system of claim 1, wherein the tissue model template library comprises a region of interest (ROI) template library providing types of ROIs required to be defined for different irradiated sites, and a material template library comprising a tissue type template library which defines corresponding tissue types for voxel units in each of the ROIs.

3. The radiotherapy system of claim 2, wherein the treatment plan module establishes a three-dimensional (3D) voxel prosthesis tissue model corresponding to the medical imaging data of the irradiated site according to the ROI template library and the tissue type template library, and simulates, through a Monte Carlo simulation program, a physical dose rate distribution when the irradiated site is irradiated by the treatment beam, according to the parameters of the treatment beam and the 3D voxel prosthesis tissue model.

4. The radiotherapy system of claim 3, wherein the material template library comprises a biological effectiveness template library defining corresponding biological effectiveness data for the voxel units in each of the ROIs, and the treatment plan module calculates an equivalent dose rate distribution when the irradiated site is irradiated by the treatment beam, according to the simulated physical dose rate distribution and biological effectiveness data of the 3D voxel prosthesis tissue model.

5. The radiotherapy system of claim 3, wherein the radiotherapy system is a boron neutron capture therapy (BNCT) system, the treatment plan module defines corresponding boron concentrations for the voxel units in each of the ROIs, and simulates, through the Monte Carlo simulation program, a boron dose ($D_B$), a fast neutron dose ($D_f$), a thermal neutron dose ($D_{th}$) and a photon dose ($D_\gamma$) of the 3D voxel prosthesis tissue model per unit time.

6. The radiotherapy system of claim 5, wherein the material template library further comprises a boron concentration ratio template library defining corresponding ratios of tissue boron concentration to blood boron concentration for the voxel units in each of the ROIs.

7. The radiotherapy system of claim 5, wherein the material template library comprises a biological effectiveness template library defining corresponding CBE, $RBE_f$, $RBE_{th}$ and $RBE_\gamma$ for the voxel units in each of the ROIs, and an equivalent dose rate D of the 3D voxel prosthesis tissue model is calculated by using formula 1:

$$D(Gy) = CBE(1/ppm) \times B_{con}(ppm) \times D_B(Gy) + RBE_f \times D_f(Gy) + RBE_{th} \times D_{th}(Gy) + RBE_\gamma \times D_\gamma(Gy) \quad \text{(formula 1)},$$

wherein CBE is a compound biological effectiveness of a boron-containing drug per unit concentration, $B_{con}$ is a tissue boron concentration, $RBE_f$ is a relative biological effectiveness (RBE) of a fast neutron, $RBE_{th}$ is RBE of a thermal neutron, and $RBE_\gamma$ is RBE of a photon.

8. The radiotherapy system of claim 7, wherein the treatment plan module performs an optimum selection to equivalent dose rate distributions obtained by simulation and calculation according to sampling of different irradiation angles, and selects at least one irradiation angle.

9. The radiotherapy system of claim 1, wherein the beam irradiation device further comprises a collimator, the treatment plan module has stored thereon a collimator template library at least partially defining parameters of treatment beams corresponding to different collimators.

10. A method for generating a treatment plan of a radiotherapy system, characterized in that the method comprises:

establishing a three-dimensional (3D) voxel prosthesis tissue model corresponding to medical imaging data of an irradiated site according to a tissue model template library;

defining beam parameters in a Monte Carlo simulation program, and performing dose simulation and calculation by sampling of different irradiation angles; and performing an optimum selection to the irradiation angles according to a calculation result, to generate the treatment plan.

11. The method for generating a treatment plan of claim 10, wherein the tissue model template library comprises a region of interest (ROI) template library and a tissue type template library, and establishing the 3D voxel prosthesis tissue model corresponding to medical imaging data of the irradiated site according to the tissue model template library comprises:

reading the medical imaging data of the irradiated site;
establishing a 3D medical imaging voxel model;
retrieving a ROI template library of the irradiated site, and defining or reading boundaries of ROIs provided in the ROI template library of the irradiated site;
retrieving a tissue type template library of the irradiated site, and giving tissue types of voxel units in each of the ROIs;
giving tissue boron concentrations of the voxel units in each of the ROIs; and
establishing the 3D voxel prosthesis tissue model.

12. The method for generating a treatment plan of claim 11, wherein the tissue model template library comprises a boron concentration ratio template library, and ratios of tissue boron concentration to blood boron concentration are given for the voxel units in each of the ROIs according to a boron concentration ratio template library of the irradiated site, so that tissue boron concentrations are given for the voxel units in each of the ROIs.

13. The method for generating a treatment plan of claim 11, wherein defining beam parameters in the Monte Carlo simulation program, and performing dose simulation and calculation by sampling of different irradiation angles comprises:

simulating a physical dose received by each voxel unit of the 3D voxel prosthesis tissue model per unit time under a defined beam irradiation and at a sampled irradiation angle, the physical dose comprising a boron dose ($D_B$), a fast neutron dose ($D_f$), a thermal neutron dose ($D_{th}$) and a photon dose ($D_\gamma$); and calculating an equivalent dose rate $\dot{D}$ of each voxel unit of the 3D voxel prosthesis tissue model per unit time under the defined beam irradiation by using formula 1:

$$D(Gy)=\text{CBE}(1/\text{ppm}) \times B_{con}(\text{ppm}) \times D_B(Gy) + \text{RBE}_f \times D_f(Gy) + \text{RBE}_{th} \times D_{th}(Gy) + \text{RBE}_\gamma \times D_\gamma(Gy) \quad \text{(formula 1)},$$

wherein CBE is a compound biological effectiveness of a boron-containing drug per unit concentration, $B_{con}$ is a tissue boron concentration, $\text{RBE}_f$ is a relative biological effectiveness (RBE) of a fast neutron, $\text{RBE}_{th}$ is RBE of a thermal neutron, and $\text{RBE}_\gamma$ is RBE of a photon, the tissue model template library comprises a biological effectiveness template library, and CBE, $\text{RBE}_f$, $\text{RBE}_{th}$ and $\text{RBE}_\gamma$ are given for the voxel units in each of the ROIs according to a biological effectiveness template library of the irradiated site.

14. The method for generating a treatment plan of claim 13, further comprising: performing an optimum selection to equivalent dose rate $\dot{D}$ distributions obtained by simulation and calculation according to sampling of different irradiation angles, and selecting at least one irradiation angle.

15. The method for generating a treatment plan of claim 10, wherein the radiotherapy system further comprises a collimator, and beam parameters corresponding to different collimators are defined in the Monte Carlo simulation program according to a collimator template library.

* * * * *